United States Patent
Sakanishi

(10) Patent No.: US 8,563,493 B2
(45) Date of Patent: *Oct. 22, 2013

(54) OIL COMPOSITION FOR COSMETICS

(75) Inventor: Yuichi Sakanishi, Ohtake (JP)

(73) Assignee: Daicel Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/499,513

(22) PCT Filed: Sep. 16, 2010

(86) PCT No.: PCT/JP2010/066058
§ 371 (c)(1),
(2), (4) Date: Mar. 30, 2012

(87) PCT Pub. No.: WO2011/040254
PCT Pub. Date: Apr. 7, 2011

(65) Prior Publication Data
US 2012/0184476 A1    Jul. 19, 2012

(30) Foreign Application Priority Data
Oct. 1, 2009    (JP) .................. 2009-229176

(51) Int. Cl.
*A61Q 1/00* (2006.01)
*A61Q 19/10* (2006.01)
*A61K 8/33* (2006.01)
*C11D 1/72* (2006.01)

(52) U.S. Cl.
USPC ........... 510/130; 510/153; 510/155; 510/159; 510/421; 510/437; 510/466; 424/401; 424/70.19; 424/70.31

(58) Field of Classification Search
USPC ......... 510/130, 153, 155, 159, 421, 437, 466; 424/401, 70.19, 70.31
See application file for complete search history.

(56) References Cited

U.S. PATENT DOCUMENTS

| | | |
|---|---|---|
| 2007/0116663 A1 | 5/2007 | Iwanaga et al. |
| 2009/0239956 A1 | 9/2009 | Sakanishi |
| 2010/0016199 A1 | 1/2010 | Sakanishi |
| 2010/0062960 A1 | 3/2010 | Sakanishi |

FOREIGN PATENT DOCUMENTS

| | | | |
|---|---|---|---|
| EP | 1709952 A1 | | 10/2006 |
| EP | 2103298 A1 | | 9/2009 |
| EP | 2145946 A1 | | 1/2010 |
| EP | 2163237 A2 | | 3/2010 |
| JP | 62-204839 A | | 9/1987 |
| JP | 4-5213 A | | 1/1992 |
| JP | 8-143420 A | | 6/1996 |
| JP | 2005-162691 A | | 6/2005 |
| JP | 2006-347896 | * | 12/2006 |
| JP | 2006-347896 A | | 12/2006 |
| JP | 2006-347900 A | | 12/2006 |
| JP | 2007-23025 A | | 2/2007 |
| JP | 2009-227593 A | | 10/2009 |
| JP | 2010-24152 A | | 2/2010 |
| JP | 2010-64977 A | | 3/2010 |

OTHER PUBLICATIONS

International Search Report issued in PCT/JP2010/066058, dated Dec. 21, 2010.

* cited by examiner

*Primary Examiner* — Brian P Mruk
(74) *Attorney, Agent, or Firm* — Birch, Stewart, Kolasch & Birch, LLP

(57) ABSTRACT

Provided are: an oil composition for cosmetics which is readily miscible with a makeup stain and can rinse out freshly through washing with water without leaving oily feeling, regardless of whether the skin is wet or not, and excels in safety and temporal stability; and a cleansing cosmetic containing the oil composition for cosmetics. The oil composition for cosmetics contains 1 to 30 percent by weight of a medium-chain polyglycerol monoalkyl ether; 1 to 30 percent by weight of a long-chain polyglycerol monoalkyl ether; and 40 to 98 percent by weight of at least one oily ingredient selected from the group consisting of silicone oils, ester oils, and triglycerols.

2 Claims, No Drawings

OIL COMPOSITION FOR COSMETICS

TECHNICAL FIELD

The present invention relates to an oil composition for cosmetics which is useful as a cleansing cosmetic for the removal of oily cosmetics.

BACKGROUND ART

In the area of cosmetics, there is a wide variety of cleansing cosmetics for removing makeup, including cleansing cosmetics containing large amounts of oils (oil components), such as those in the form of creams, milky lotions, oils, and oily gels; and cleansing cosmetics containing none or trace amounts of oils, such as those in the form of lotions and aqueous gels.

The cleansing cosmetics containing large amounts of oils, through having excellent detergency (cleansing power), are sticky due to residual oily ingredients even after rinsing, and thereby need another cleansing typically with a facial cleansing agent. In addition, they are not suitable for use in a bathroom, because they have poor detergency and give poor feeling upon use when the skin is wet. Independently, the cleansing cosmetics containing none or trace amounts of oils have weak detergency, although they less give sticky feeling (oily feeling) after rinsing.

To solve these problems, there have been reported aqueous gel detergents each including a polyoxyethylene fatty acid ester (see, for example, Patent Literature (PTL) 1 and 2). The aqueous gel detergents, however, not only have insufficient detergency but also suffer from a safety problem of the polyoxyethylene fatty acid ester. In addition, they have poor storage stability because of having a fatty acid moiety in the molecule.

As a possible solution to the safety problem, there have been investigated cleansing cosmetics including a polyglyceryl fatty acid ester or a polyglycerol monoalkyl ether (see, for example, PTL 3 and 4). However, the cleansing cosmetic including a polyglyceryl fatty acid ester suffers from poor temporal stability, because the polyglyceryl fatty acid ester is liable to be hydrolyzed in a system containing water (water-incorporated system). As the cleansing cosmetic including a polyglycerol monoalkyl ether, there is known a water-incorporated cleansing cosmetic, but this forms neither lamellar liquid crystal phase nor bicontinuous microemulsion and has insufficient detergency.

Recently, a technique for forming a bicontinuous microemulsion including an oily phase and an aqueous phase both being continuous has been developed by using a specific polyglyceryl fatty acid ester (PTL 5). This technique has been developed as a technique for solving the drawbacks of oily cleansing cosmetics, i.e., the problems of poor detergency and poor feeling upon use when the skin is wet. However, the polyglyceryl fatty acid ester is a complex mixture containing an unintended multisubstituted substance and a polyglycerol derivative having no hydrophobic group, thereby has a low surfactant potency, and should be added in a large amount so as to form a bicontinuous microemulsion and to exhibit sufficient detergency. This may increase irritation to the skin and may cause inflammation.

CITATION LIST

Patent Literature

PTL 1: Japanese Unexamined Patent Application Publication (JP-A) No. H04-5213

PTL 2: Japanese Unexamined Patent Application Publication (JP-A) No. H08-143420

PTL 3: Japanese Unexamined Patent Application Publication (JP-A) No. 2007-23025

PTL 4: Japanese Unexamined Patent Application Publication (JP-A) No. 2006-347900

PTL 5: Japanese Unexamined Patent Application Publication (JP-A) No. 2005-162691

SUMMARY OF INVENTION

Technical Problem

Accordingly, an object of the present invention is to provide an oil composition for cosmetics which is readily miscible with a makeup stain and can rinse out freshly through washing with water without leaving oily feeling, regardless of whether the skin is wet or not, and excels in safety and temporal stability. Another object of the present invention is to provide a cleansing cosmetic containing the oil composition for cosmetics.

Solution to Problem

After intensive investigations to achieve the objects, the present inventors have found that an oil composition for cosmetics, containing specific polyglycerol monoalkyl ethers in specific contents, excels in safety and temporal stability and is capable of forming a bicontinuous microemulsion when mixed with water. The present invention has been made based on these findings.

Specifically, the present invention provides, in an aspect, an oil composition for cosmetics, which contains 1 to 30 percent by weight of a medium-chain polyglycerol monoalkyl ether represented by following Formula (1):

$$R_1O-(C_3H_6O_2)n_1-H \qquad (1)$$

wherein $R_1$ represents a linear aliphatic hydrocarbon group having 6 to 11 carbon atoms, or a branched-chain aliphatic hydrocarbon group having 6 to 14 carbon atoms; and $n_1$ denotes an average degree of glycerol polymerization and is from 1.5 to 4;

1 to 30 percent by weight of a long-chain polyglycerol monoalkyl ether represented by following Formula (2):

$$R_2O-(C_3H_6O_2)n_2-H \qquad (2)$$

wherein $R_2$ represents a linear aliphatic hydrocarbon group having 12 to 18 carbon atoms, or a branched-chain aliphatic hydrocarbon group having 16 to 22 carbon atoms; and $n_2$ denotes an average degree of glycerol polymerization and is from 1.5 to 4; and 40 to 98 percent by weight of at least one oily ingredient selected from the group consisting of silicone oils, ester oils, and triglycerols.

The present invention provides, in another aspect, a cleansing cosmetic containing the oil composition for cosmetics.

Advantageous Effects of Invention

The oil composition for cosmetics according to the present invention contains specific polyglycerol monoalkyl ethers as surfactants and is capable of forming a bicontinuous microemulsion when mixed with water. The oil composition, even when used to a wet skin, is rapidly miscible with a makeup stain, spaces the stain from the skin, and washes the stain away with water without leaving oily feeling. The cleansing cosmetic according to the present invention contains the oil composition for cosmetics, can thereby be used even in a bathroom, excels in detergency and feeling upon use, and is particularly useful as a detergent for removing oily cosmetics.

DESCRIPTION OF EMBODIMENTS

An oil composition for cosmetics according to the present invention contains 1 to 30 percent by weight of a medium-chain polyglycerol monoalkyl ether represented by following Formula (1):

$$R_1O-(C_3H_6O_2)n_1-H \qquad (1)$$

wherein $R_1$ represents a linear aliphatic hydrocarbon group having 6 to 11 carbon atoms, or a branched-chain aliphatic hydrocarbon group having 6 to 14 carbon atoms; and $n_1$ denotes an average degree of glycerol polymerization and is from 1.5 to 4;
1 to 30 percent by weight of a long-chain polyglycerol monoalkyl ether represented by following Formula (2):

$$R_2O-(C_3H_6O_2)n_2-H \qquad (2)$$

wherein $R_2$ represents a linear aliphatic hydrocarbon group having 12 to 18 carbon atoms, or a branched-chain aliphatic hydrocarbon group having 16 to 22 carbon atoms; and $n_2$ denotes an average degree of glycerol polymerization and is from 1.5 to 4; and
40 to 98 percent by weight of at least one oily ingredient selected from the group consisting of silicone oils, ester oils, and triglycerols.

[Medium-Chain Polyglycerol Monoalkyl Ether]

The medium-chain polyglycerol monoalkyl ether for use in the present invention is represented by following Formula (1), in which $R_1$ represents a linear aliphatic hydrocarbon group having 6 to 11 carbon atoms or a branched-chain aliphatic hydrocarbon group having 6 to 14 carbon atoms; and $n_1$ denotes an average degree of glycerol polymerization and is from 1.5 to 4.

$$R_1O-(C_3H_6O_2)n_1-H \qquad (1)$$

The moiety $C_3H_6O_2$ in the parentheses in Formula (1) has both structures represented by following Formulae (3) and (4):

$$-CH_2-CHOH-CH_2O- \qquad (3)$$

$$-CH(CH_2OH)CH_2O- \qquad (4)$$

$R_1$ represents a linear aliphatic hydrocarbon group having 6 to 11 carbon atoms, or a branched-chain aliphatic hydrocarbon group having 6 to 14 carbon atoms. Examples of the linear aliphatic hydrocarbon group having 6 to 11 carbon atoms include linear (normal) alkyl groups each having 6 to 11 carbon atoms, such as n-hexyl, n-heptyl, n-octyl, n-nonyl, n-decyl, and n-undecyl groups; and linear alkenyl groups each having 6 to 11 carbon atoms, such as n-hexenyl, n-decenyl, and n-undecenyl. Examples of the branched-chain aliphatic hydrocarbon group having 6 to 14 carbon atoms include branched alkyl groups each having 6 to 14 carbon atoms, such as methylpentyl, ethylpentyl, methylhexyl, ethylhexyl, methylheptyl, ethylheptyl, propylheptyl, butyloctyl, isononyl, s-nonyl, t-nonyl, isodecyl, s-decyl, t-decyl, isolauryl, s-lauryl, t-lauryl, isomyristyl, s-myristyl, t-myristyl, isocetyl, s-cetyl, and t-cetyl; and branched alkenyl groups each having 6 to 14 carbon atoms, such as isooctenyl, s-octenyl, t-octenyl, isodecenyl, s-decenyl, t-decenyl, isoundecenyl, s-undecenyl, t-undecenyl, isododecenyl, s-dodecenyl, t-dodecenyl, isotridecenyl, s-tridecenyl, t-tridecenyl, isotetradecenyl, s-tetradecenyl, and t-tetradecenyl.

Among them, a linear alkyl group having 8 to 10 carbon atoms or a branched-chain alkyl group having 8 to 12 carbon atoms is preferred as $R_1$ from the viewpoint of cost and suitable inhibition of liquid crystal formation, of which octyl, nonyl, isononyl, decyl, or octylbutyl group is particularly preferred.

The number $n_1$ denotes an average degree of glycerol polymerization and is from 1.5 to 4 (preferably from 1.5 to 2.5). A medium-chain polyglycerol monoalkyl ether having $n_1$ of lower than the above-specified range may cause the oil composition to have insufficient water solubility. In contrast, a medium-chain polyglycerol monoalkyl ether having $n_1$ of higher than the above-specified range may tend to cause the oil composition to have excessively high water solubility and insufficient oil solubility.

Exemplary medium-chain polyglycerol monoalkyl ethers for use in the present invention include diglycerol monooctyl ether, diglycerol monononyl ether, diglycerol monoisononyl ether, diglycerol monodecyl ether, diglycerol monooctylbutyl ether, and tetraglycerol monooctylbutyl ether. Each of them may be used alone or in combination.

[Long-Chain Polyglycerol Monoalkyl Ether]

The long-chain polyglycerol monoalkyl ether for use in the present invention is represented by following Formula (2), in which $R_2$ represents a linear aliphatic hydrocarbon group having 12 to 18 carbon atoms, or a branched-chain aliphatic hydrocarbon group having 16 to 22 carbon atoms; and $n_2$ denotes an average degree of glycerol polymerization and is from 1.5 to 4. The moiety $C_3H_6O_2$ in the parentheses has both structures represented by Formulae (3) and (4).

$$R_2O-(C_3H_6O_2)n_2-H \qquad (2)$$

$R_2$ represents a linear aliphatic hydrocarbon group having 12 to 18 carbon atoms, or a branched-chain aliphatic hydrocarbon group having 16 to 22 carbon atoms. Examples of the linear aliphatic hydrocarbon group having 12 to 18 carbon atoms include linear alkyl groups each having 12 to 18 carbon atoms, such as n-dodecyl, n-tridecyl, n-tetradecyl, n-pentadecyl, n-hexadecyl, n-heptadecyl, and n-octadecyl groups; and linear alkenyl groups each having 12 to 18 carbon atoms, such as n-dodecenyl, n-tridecenyl, n-tetradecenyl, n-pentadecenyl, n-hexadecenyl, n-heptadecenyl, and n-octadecenyl groups. Examples of the branched-chain aliphatic hydrocarbon group having 16 to 22 carbon atoms include branched alkyl groups each having 16 to 22 carbon atoms, such as isohexadecyl, s-hexadecyl, t-hexadecyl, isoheptadecyl, s-heptadecyl, t-heptadecyl, isooctadecyl, s-octadecyl, t-octadecyl, isononadecyl, s-nonadecyl, t-nonadecyl, isoicosyl, s-icosyl, t-icosyl, isoeicosyl, s-eicosyl, t-eicosyl, isohenicosyl, s-henicosyl, t-henicosyl, isodocosyl, s-docosyl, and t-docosyl; and branched alkenyl groups each having 16 to 22 carbon atoms, such as isohexadecenyl, s-hexadecenyl, t-hexadecenyl, isoheptadecenyl, s-heptadecenyl, t-heptadecenyl, isooctadecenyl, s-octadecenyl, t-octadecenyl, isononadecenyl, s-nonadecenyl, t-nonadecenyl, isoicosenyl, s-icosenyl, t-icosenyl, isoeicosenyl, s-eicosenyl, t-eicosenyl, isohenicosenyl, s-henicosenyl, t-henicosenyl, isodocosenyl, s-docosenyl, and t-docosenyl.

Among them, a linear alkyl group having 14 to 18 carbon atoms or a branched-chain alkyl group having 16 to 22 carbon atoms is preferred as the long-chain polyglycerol monoalkyl ether for use in the present invention, of which myristyl, palmityl, palmitoyl, stearyl, or oleyl group is particularly preferred, because of having high liquid crystal formability.

The number $n_2$ denotes an average degree of glycerol polymerization and is from 1.5 to 4 (preferably from 1.5 to 2.5). A long-chain polyglycerol monoalkyl ether having $n_2$ of lower than the above-specified range may cause the oil composition to have insufficient water solubility. In contrast, a long-chain polyglycerol monoalkyl ether having $n_2$ of higher than the above-specified range may tend to cause the oil composition to have excessively high water solubility and insufficient oil solubility.

Exemplary long-chain polyglycerol monoalkyl ethers for use in the present invention include diglycerol monomyristyl ether, diglycerol monopalmityl ether, diglycerol monopalmitoyl ether, diglycerol monostearyl ether, diglycerol monooleyl ether, triglycerol monomyristyl ether, triglycerol monopalmityl ether, triglycerol monopalmitoyl ether, triglycerol monostearyl ether, triglycerol monooleyl ether, tetraglycerol monomyristyl ether, tetraglycerol monopalmityl ether, tetraglycerol monopalmitoyl ether, tetraglycerol monostearyl ether, and tetraglycerol monooleyl ether. Each of them may be used alone or in combination.

Exemplary methods for producing the medium-chain or long-chain polyglycerol monoalkyl ether include, but are not limited to, (1) a method of adding glycidol to an aliphatic alcohol in such an amount that the ratio (molar ratio) of the aliphatic alcohol to glycidol be a specific value, and reacting them in the presence of a basic catalyst; (2) a method of reacting a polyglycerol with an α-olefin epoxide; and (3) a method of ring-opening an alkyl glycidyl ether using a polyglycerol in the presence of an acid catalyst or an alkali catalyst. Among them, the method (1) is preferred in the present invention, from the viewpoint of the presence or absence of the formation of impurities.

In the present invention, the alkoxy group ($R_1O$—) in the medium-chain polyglycerol monoalkyl ether has the function of inhibiting liquid crystal formation, whereas the alkoxy group ($R_2O$—) in the long-chain polyglycerol monoalkyl ether has the function of promoting liquid crystal formation. By regulating the contents of the medium-chain polyglycerol monoalkyl ether and the long-chain polyglycerol monoalkyl ether, a stable bicontinuous microemulsion can be formed.

The medium-chain polyglycerol monoalkyl ether is contained in the oil composition for cosmetics in a content of from 1 to 30 percent by weight, and preferably from 1 to 20 percent by weight for good cost and satisfactory formation of a bicontinuous microemulsion. The medium-chain polyglycerol monoalkyl ether, if contained in a content out of the above-specified range, may impede the formation of a bicontinuous microemulsion and may thereby cause the oil composition for cosmetics to have insufficient solubilizing power in water. In addition, the medium-chain polyglycerol monoalkyl ether, if contained in a content lower than the above-specified range, may cause an excessively hard gel.

The long-chain polyglycerol monoalkyl ether is contained in the oil composition for cosmetics in a content of from 1 to 30 percent by weight, and preferably from 1 to 20 percent by weight for good cost and satisfactory formation of a bicontinuous microemulsion. The long-chain polyglycerol monoalkyl ether, if contained in a content out of the above-specified range, may impede the formation of a bicontinuous microemulsion and may cause the oil composition for cosmetics to have insufficient solubilizing power (solubility) in water. In addition, the long-chain polyglycerol monoalkyl ether, if contained in a content of higher than the above-specified range, may cause an excessively hard gel.

The compositional ratio of the medium-chain polyglycerol monoalkyl ether to the long-chain polyglycerol monoalkyl ether in the oil composition for cosmetics is typically from about 5/95 to about 95/5, preferably from 10/90 to 90/10, and particularly preferably from 20/80 to 80/20. The oil composition for cosmetics, if having a compositional ratio of the medium-chain polyglycerol monoalkyl ether to the long-chain polyglycerol monoalkyl ether out of the above-specified range, may fail to form a bicontinuous microemulsion and may have insufficient solubilizing power in water.

[Oily Ingredient]

The oil composition for cosmetics according to the present invention contains at least one oily ingredient selected from the group consisting of silicone oils, ester oils, and triglycerols.

Exemplary silicone oils include methylpolysiloxanes, methylphenylpolysiloxanes, methylcyclopolysiloxanes, decamethylcyclopentasiloxanes, polyether-modified silicones, amino-modified silicones, betaine-modified silicones, alkyl-modified silicones, and alkoxy-modified silicones. Each of them may be used alone or in combination.

Exemplary ester oils include diisopropyl adipate, diisobutyl adipate, dioctyl adipate, di(2-hexyldecyl)adipate, diisostearyl adipate, isostearyl myristate, isotridecyl myristate, isopropyl myristate, octyldodecyl myristate, cetyl octanoate, isononyl isononanoate, isodecyl isononanoate, isotridecyl isononanoate, diisopropyl sebacate, isopropyl palmitate, hexyl laurate, decyl oleate, hexyldecyl dimethyloctanoate, octyl palmitate, lauryl lactate, octyldodecyl lactate, isocetyl stearate, isocetyl isostearate, ethylene glycol dioctanoate, dipentaerythritol fatty acid esters, cetyl caprylate, glyceryl tricaprylate, neopentyl glycol dicaprylate, and diisostearyl malate. Each of them may be used alone or in combination.

Exemplary triglycerols include liquid oils such as avocado oil, camellia oil, turtle oil, macadamia nut oil, corn oil, mink oil, olive oil, rapeseed oil, yolk oil, sesame oil, persic oil, wheat germ oil, sasanqua oil, castor oil, linseed oil, safflower oil, cotton seed oil, perilla oil, soybean oil, peanut oil, tea seed oil, torreya oil, rice bran oil, Chinese tung oil, Japanese tung oil, jojoba oil, germ oil, glyceryl trioctanoate, and glyceryl triisopalmitate; hydrocarbons such as liquid paraffin, squalene, squalane, and pristane; and higher alcohols such as oleic acid, tall oil, and isostearic acid. Each of them may be used alone or in combination.

The oily ingredient is contained in the composition in a content of from 40 to 98 percent by weight, and preferably from about 60 to about 98 percent by weight, based on the total amount of the composition. If the oily ingredient is contained in a content lower than the above-specified range, the surfactants may be contained in relatively higher contents and may thereby cause increased irritation typically to the skin. In contrast, if the oily ingredient is contained in a content higher than the above-specified range, the surfactants may be contained in relatively lower contents, and this may cause the oily ingredient to be less resistant to water and may tend to form an oil-in-water (O/W) emulsion in the presence of water, thus resulting in significantly reduced detergency.

Oil compositions for cosmetics according to the present invention are usable typically as detergents for removing oil stains, cleansing cosmetics for removing oily cosmetics, suntan oils, baby oils, hair oils, and foamy massage oils, and, above all, are advantageously usable as cleansing cosmetics typically for removing oily cosmetics.

[Cleansing Cosmetics]

A cleansing cosmetic according to the present invention contains the oil composition for cosmetics. The cleansing cosmetic may be in any form not limited, such as a lotion, solution, milky lotion, cream, gel, or oil, but is preferably in the form of a cream, gel, or oil for satisfactory feeling upon use.

The cleansing cosmetic may further contain a polyhydric alcohol as a humectant. Exemplary polyhydric alcohols include glycerol, diglycerol, maltitol, 1,3-butylene glycol, isoprene glycol, dipropylene glycol, polyethylene glycols, pentaerythritol, neopentyl glycol, sorbitol, sorbitan, trehalose, and propylene glycol. Each of them may be used alone or in combination. Among them, the cleansing cosmetic according to the present invention preferably contains at least one selected from the group consisting of glycerol, maltitol, 1,3-butylene glycol, propylene glycol, and sorbitol. Such polyhydric alcohol may be contained in the cleansing cosmetic in a content of typically from 5 to 70 percent by weight, and preferably from 10 to 50 percent by weight.

The cleansing cosmetic according to the present invention may further contain one or more suitable additional components according to necessity, within ranges capable of achieving the objects of the present invention. Exemplary additional components include nonionic surfactants other than the polyglycerol monoalkyl ethers; anionic surfactants; amphoteric surfactants; lower alcohols; powders; antioxidants; antioxidation assistants; ultraviolet absorbers; humectants other than the polyhydric alcohols; antiinflammatory agents; antiseptic agents; pH adjusters; extracts derived from animals, vegetables (plants), fishery products, and microorganisms; and flavors.

Though not limited, examples of nonionic surfactants other than the polyglycerol monoalkyl ethers include surfactants such as glyceryl fatty acid esters, polyglyceryl fatty acid esters, polyalkylene glycol fatty acid esters, sorbitan fatty acid esters, sugar fatty acid esters, pentaerythritol fatty acid esters, polyoxyalkylene hydrogenated caster oil fatty acid esters, fatty acid alkanolamides, polyoxyalkylene glycols, esters between a polyoxyalkylene glycol and a monohydric or polyhydric alcohol, polyoxyalkylene sugar ethers, condensates between a fatty amide and a polyoxyalkylene glycol, condensates between an aliphatic amine and a polyoxyalkylene glycol, and alkyl or alkenyl polyglycosides.

Exemplary anionic surfactants include, but are not limited to, polyoxyethylene alkyl ether sulfates, salts of alkyl sulfates, alkylbenzenesulfonic acid salts, α-olefinsulfonic acid salts, glutamic acid and other amino acid surfactants, N-acylmethyltarric acid salts, and salts of alkyl phosphates.

Exemplary amphoteric surfactants included, but are not limited to, carboxybetaine-, imidazolimium-, sulfobetaine-, and alanine-type amphoteric surfactants.

Exemplary lower alcohols include, but not limited to, ethanol, propyl alcohol, ethylene glycol, and diethylene glycol.

The powder components (powders) are not limited and include, for example, inorganic powders and organic powders. Exemplary inorganic powders include talc, kaolin, mica, sericite, muscovite, phlogopite, synthetic mica, lepidolite, biotite, lithia mica, vercumulite, magnesium carbonate, zirconium silicate, aluminum silicate, barium silicate, calcium silicate, zinc silicate, magnesium silicate, strontium silicate, metal salts of tungstic acid, magnesium, silica, zeolite, barium sulfate, calcined calcium sulfate (calcined gypsum), calcium phosphate, fluoroapatite, hydroxyapatite, ceramic powders, activated carbon, medical carbon, metal soaps (e.g., zinc myristate, calcium palmitate, and aluminum stearate), and boron nitride. Exemplary organic powders include polyamide resin powders (nylon powders), polyethylene powders, poly(methyl methacrylate) powders, polystyrene powders, powders of copolymer resins between styrene and acrylic acid, benzoguanamine resin powders, and cellulose powders.

Exemplary antioxidants include, but are not limited to, vitamin E, dibutylhydroxytoluene, butylhydroxyanisole, and gallic acid esters.

Exemplary antioxidation assistants include, but are not limited to, ascorbic acid, phytic acid, kephalin, and maleic acid.

Exemplary ultraviolet absorbers include, but are not limited to, benzophenone derivatives such as 2-hydroxy-4-methoxybenzophenone, 2-hydroxy-4-methoxybenzophenone-5-sulfonic acid, 2-hydroxy-4-methoxybenzophenone-5-sulfonic acid salts, and dihydroxydimethoxybenzophenone; p-aminobenzoic acid derivatives such as p-aminobenzoic acid and ethyl p-aminobenzoate; methoxycinnmaic acid derivatives such as ethyl p-methoxycinnamate, isopropyl p-methoxycinnamate, and octyl p-methoxycinnamate; salicylic acid derivatives such as octyl salicylate and phenyl salicylate; as well as urocanic acid, urocanic acid derivatives, 4-tert-butyl-4'-methoxydibenzoylmethane, 2-(hydroxy-5'-methylphenyl)benzotriazole, and methyl anthranilate.

Exemplary humectants other than the polyhydric alcohols include sodium lactate, pyrrolidonecarboxylic acid, and pyrrolidonecarboxylic acid derivatives.

Exemplary anti-inflammatory agents include, but are not limited to glycyrrhizic acid, glycyrrhizic acid derivatives, glycyrrhetic acid, glycyrrhetic acid derivatives, allantoin, hydrocortisone acetate, and azulene.

Exemplary antiseptic agents include, but are not limited to, methylparaben, propyparaben, and phenoxyethanol.

Examples of the pH adjusters include, but are not limited to, citric acid, hydrochloric acid, sulfuric acid, phosphoric acid, sodium hydroxide, and ammonia.

Examples of the extracts derived from animals, vegetables (plants), fishery products, and microorganisms include, but are not limited to, extracts such as tea extract, aloe extract, ginkgo extract, swertia herb extract, mugwort extract, garlic extract, Scutellaria root extract, rosemary extract, sponge gourd extract, placental extract, extract from lactic acid bacteria culture, and seaweed extract.

Flavors for use herein are not specifically limited, as long as being those generally used in cosmetics.

The cleansing cosmetic according to the present invention, as containing the oil composition for cosmetics, is readily miscible with a makeup stain regardless of whether the skin is wet or not, can be rinse out (wash away) freshly by washing with water without leaving oily feeling, and can be suitably used even in a bathroom. In addition, the cleansing cosmetic excels also in safety and temporal stability.

EXAMPLES

The present invention will be illustrated in further detail with reference to several working examples below. It should be noted, however, that these examples are never construed to limit the scope of the present invention.

Examples 1 to 7

Comparative Examples 1 to 9

A series of oil compositions for cosmetics having the blending compositions given in Table 1 below was prepared according to a customary procedure, and evaluations were made on them according to the following criteria.
(Evaluation Methods and Criteria)
(1) Detergency (Under Dry Condition)
A lipstick (trade name "SOFINA AUBE couture Designing Stay Rouge RD532", supplied by Kao Corporation) was applied to the forearm; about 0.5 g of each of the oil compositions for cosmetics obtained in Examples 1 to 7 and Comparative Examples 1 to 9 was taken in the hand and sufficiently mixed with the lipstick by massaging the applied portion twenty times. How the applied lipstick was removed after massaging was visually observed, and the detergency was evaluated according to the following criteria.

<Criteria>
Excellent: The lipstick was completely removed
Good: Almost all of the lipstick was removed
Fair: The lipstick slightly remained
Poor: Almost no lipstick was removed (2) Detergency (Under Wet Condition)

A lipstick (trade name "SOFINA AUBE couture Designing Stay Rouge RD532", Kao Corporation) was applied to the forearm; the applied portion of the forearm was wetted with water; about 0.5 g of each of the oil compositions for cosmetics obtained in Examples 1 to 7 and Comparative Examples 1 to 9 was taken in the hand and sufficiently mixed with the lipstick by massaging the applied portion twenty times. How the applied lipstick was removed after massaging was visually observed, and the detergency was evaluated according to the aforementioned criteria.

(3) Solubilizing Power

Each of the oil compositions for cosmetics obtained in Examples 1 to 7 and Comparative Examples 1 to 9 (0.5 g) was combined and thoroughly mixed with 2 g of water to give a mixture, whether the mixture was transparent or not was visually observed, and the solubilizing power was evaluated according to the following criteria.

<Criteria>
Good: Transparent
Poor: Opaque

As is demonstrated by Table 1, the oil compositions for cosmetics according to the present invention are rapidly miscible with a makeup stain and exhibit satisfactory cleansing power when the skin is wet, or not. In addition, they have satisfactory solubility in water, can thereby be rinsed out through washing with water rapidly and without leaving oily feeling, and excel in feeling upon use.

INDUSTRIAL APPLICABILITY

The oil compositions for cosmetics according to the present invention, as containing specific polyglycerol monoalkyl ethers as surfactants, can form a bicontinuous microemulsion when mixed with water. When used, they are rapidly miscible with a makeup stain and space the stain from the skin even when the skin is wet, and can rinse out through washing with water without leaving oily feeling. The cleansing cosmetics according to the present invention, as containing the oil compositions for cosmetics, can be used even in a bathroom, excel in detergency and feeling upon use, and are particularly useful as detergents for removing oily cosmetics.

The invention claimed is:
1. An oil composition for cosmetics, comprising:
1 to 30 percent by weight of a medium-chain polyglycerol monoalkyl ether represented by following Formula (1):

$$R_1O\text{—}(C_3H_6O_2)n_1\text{-}H \tag{1}$$

TABLE 1

| Components | Examples (percent by weight) | | | | | | |
|---|---|---|---|---|---|---|---|
| | 1 | 2 | 3 | 4 | 5 | 6 | 7 |
| Cetyl octanoate | 70 | 50 | 50 | 70 | 70 | 70 | 70 |
| Liquid paraffin | | 20 | | | | | |
| Decamethylcyclopentanesiloxane | | | 20 | | | | |
| Diglycerol monooctyl ether | 12 | 12 | 12 | | | 15 | 15 |
| Diglycerol monodecyl ether | | | | 16.5 | | | |
| Tetraglycerol monooctylbutyl ether | | | | | 12 | | |
| Diglycerol monooleyl ether | 18 | 18 | 18 | 13.5 | 18 | | |
| Diglycerol monomyristyl ether | | | | | | 15 | |
| Diglycerol monopalmityl ether | | | | | | | 15 |
| Diglyceryl monooctanoate | | | | | | | |
| Diglyceryl monodecanoate | | | | | | | |
| Diglyceryl monooleate | | | | | | | |
| Evaluation Detergency Under dry condition | Excellent | Excellent | Excellent | Excellent | Good | Good | Good |
| Under wet condition | Excellent | Excellent | Excellent | Excellent | Good | Excellent | Good |
| Solubilizing power | Good | Good | Good | Good | Good | Good | Good |

| Components | Comparative Examples (percent by weight) | | | | | | | | |
|---|---|---|---|---|---|---|---|---|---|
| | 1 | 2 | 3 | 4 | 5 | 6 | 7 | 8 | 9 |
| Cetyl octanoate | 70 | 70 | 70 | 70 | 70 | 70 | 70 | 70 | 50 |
| Liquid paraffin | | | | | | | | | 20 |
| Decamethylcyclopentanesiloxane | | | | | | | | | |
| Diglycerol monooctyl ether | 30 | | | | | | | | |
| Diglycerol monodecyl ether | | 30 | | | | | | | |
| Tetraglycerol monooctylbutyl ether | | | 30 | | | | | | |
| Diglycerol monooleyl ether | | | | 30 | | | | | |
| Diglycerol monomyristyl ether | | | | | 30 | | | | |
| Diglycerol monopalmityl ether | | | | | | 30 | | | |
| Diglyceryl monooctanoate | | | | | | | 12 | | 12 |
| Diglyceryl monodecanoate | | | | | | | | 12 | |
| Diglyceryl monooleate | | | | | | | 18 | 18 | 18 |
| Evaluation Detergency Under dry condition | Poor | Poor | Poor | Poor | Poor | Poor | Good | Good | Good |
| Under wet condition | Poor | Poor | Poor | Fair | Fair | Fair | Fair | Poor | Poor |
| Solubilizing power | Poor | Poor | Poor | Poor | Poor | Poor | Poor | Poor | Poor | wherein $R_1$ represents a linear aliphatic hydrocarbon group having 6 to 10 carbon atoms, or a branched-chain aliphatic hydrocarbon group having 6 to 14 carbon atoms; and $n_1$ denotes an average degree of glycerol polymerization and is from 1.5 to 4;

1 to 30 percent by weight of a long-chain polyglycerol monoalkyl ether represented by following Formula (2):

$$R_2O\text{---}(C_3H_6O_2)n_2\text{-H} \qquad (2)$$

wherein $R_2$ represents a linear aliphatic hydrocarbon group having 14 to 18 carbon atoms, or a branched-chain aliphatic hydrocarbon group having 16 to 22 carbon atoms; and $n_2$ denotes an average degree of glycerol polymerization and is from 1.5 to 4; and 40 to 98 percent by weight of at least one oily ingredient selected from the group consisting of silicone oils, ester oils, avocado oil, camellia oil, turtle oil, macadamia nut oil, corn oil, mink oil, olive oil, rapeseed oil, yolk oil, sesame oil, persic oil, wheat germ oil, sasanqua oil, castor oil, linseed oil, safflower oil, cotton seed oil, perilla oil, soybean oil, peanut oil, tea seed oil, torreya oil, rice bran oil, Chinese tung oil, Japanese tung oil, jojoba oil, germ oil, glyceryl trioctanoate, glyceryl triisopalmitate, liquid paraffin, squalene, squalane, pristane, oleic acid, tall oil and isostearic acid.

2. A cleansing cosmetic comprising the oil composition for cosmetics of claim 1.

* * * * *